(12) United States Patent
Baccelli et al.

(10) Patent No.: US 6,585,737 B1
(45) Date of Patent: Jul. 1, 2003

(54) BACKBONE OSTEOSYNTHESIS SYSTEM WITH COLLAR AND LOCK

(75) Inventors: Christian Baccelli, Saint Médard d'Eyrans (FR); Fabien Gauchet, Duvy (FR); Cécile Vienney, Bordeaux (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/674,344

(22) PCT Filed: Apr. 29, 1999

(86) PCT No.: PCT/FR99/01021
§ 371 (c)(1),
(2), (4) Date: Mar. 13, 2001

(87) PCT Pub. No.: WO99/56652
PCT Pub. Date: Nov. 11, 1999

(30) Foreign Application Priority Data

Apr. 30, 1998 (FR) ............................................... 98 05525
Jan. 22, 1999 (FR) ............................................... 99 00703

(51) Int. Cl.$^7$ ........................................................ A61B 17/56
(52) U.S. Cl. ........................................................ 606/61
(58) Field of Search ................................ 606/61, 72, 73

(56) References Cited

U.S. PATENT DOCUMENTS

| | | | |
|---|---|---|---|
| 4,988,351 A | * | 1/1991 | Paulos et al. ................. 606/72 |
| 5,176,680 A | * | 1/1993 | Vignaud et al. ............... 606/61 |
| 5,217,497 A | * | 6/1993 | Mehdian ....................... 623/17 |
| 5,385,583 A | * | 1/1995 | Cotrel .......................... 623/17 |
| 5,536,268 A | | 7/1996 | Griss |
| 5,667,508 A | * | 9/1997 | Errico et al. .................. 606/73 |
| 5,683,390 A | * | 11/1997 | Metz-Stavenhagen et al. ............................ 606/61 |
| 5,735,853 A | * | 4/1998 | Olerud ......................... 606/71 |
| 5,738,685 A | * | 4/1998 | Halm et al. ................... 606/61 |
| 5,882,350 A | * | 3/1999 | Ralph et al. .................. 606/61 |
| 5,885,286 A | * | 3/1999 | Sherman et al. .............. 606/61 |
| 6,077,262 A | * | 6/2000 | Schlapfer et al. ............. 606/61 |
| 6,102,951 A | * | 8/2000 | Sutter et al. .................. 623/18 |
| 6,270,304 B1 | * | 8/2001 | Freedland .................... 411/392 |

FOREIGN PATENT DOCUMENTS

| | | |
|---|---|---|
| DE | 42 40 223 | 6/1994 |
| DE | 196 05 640 | 8/1997 |
| EP | 0 682 918 | 11/1995 |

* cited by examiner

Primary Examiner—Eduardo C. Robert
(74) Attorney, Agent, or Firm—Lerner, David, Littenberg, Krumholz & Mentlik, LLP (57) ABSTRACT

The invention concerns a spinal osteosynthesis system comprising a rod, a vertebral member including two branches capable of receiving the rod between them, a collar for preventing the branches from being spaced, and a lock for clamping the rod, the lock being freely rotatable on the collar. Either one of the collar or the lock is capable of receiving the other of the flange or the lock for mounting the lock on the collar.

40 Claims, 10 Drawing Sheets

FIG_5

FIG_8

FIG_9

FIG. 10

FIG_11

FIG_12

FIG_13

FIG. 14

BACKBONE OSTEOSYNTHESIS SYSTEM WITH COLLAR AND LOCK

BACKGROUND OF THE INVENTION

The invention concerns spinal osteosynthesis systems.

An osteosynthesis system comprising a pedicle screw with two branches which can receive a connecting rod between them is known from document WO 92/03100, FIG. 6. A cylindrical cap has, on its inner face, a thread which can cooperate with a thread on an outer cylindrical face of the branches for the purpose of screwing the cap onto these. A lock mounted movably in rotation on the cap can clamp the rod between the branches when the cap is screwed onto them.

SUMMARY OF THE INVENTION

An object of the invention is to make available a system of a type different than that disclosed in said document, and in particular one which allows the lock and the collar to be joined together simply and quickly.

To achieve this object, the invention provides a spinal osteosynthesis system including a rod, a vertebral member comprising two branches which can receive the rod between them, a collar which can prevent the branches from being spaced apart, and a lock which can clamp the rod and can be mounted movably in rotation on the collar, and in which either one of the collar or the lock has a groove which can receive the other of the collar or the lock for mounting the lock on the collar.

Thus, the parts are joined together using a reduced number of components, which simplifies and accelerates assembly. Moreover, the attachment of the two parts is robust and secure.

Advantageously, the collar and the lock have introduction threads for introducing the other of the collar or the lock into the groove.

Advantageously, the collar and/or the lock is elastically deformable for introducing the other of the collar or the lock into the groove.

Thus, it is very easy to join the lock and the collar together to obtain the abovementioned joining, and yet without damaging the quality and stability of the connection obtained.

Advantageously, the lock comprises at least one slot at the level of the groove.

Advantageously, a first of the collar or the lock, preferably the lock, has a tightening thread which can cooperate with a tightening thread of the branches, the second of the collar or the lock extending opposite the tightening thread of the first.

Thus, the second maintains the branches in a position exactly opposite the thread. Any spacing-apart or closing-together of the branches is therefore excluded, irrespective of the stresses tending locally to displace the branches.

Advantageously, the tightening thread of the first is one of the introduction threads.

Thus, it is possible to avoid using numerous threads. Consequently, it is possible to increase the dimensions of the thread and thereby facilitate its production without increasing the dimensions of the component by comparison.

Advantageously, the system is configured in such a way that the tightening thread extends between the groove and the rod.

Advantageously, the system is configured in such a way that the groove extends between the rod and the tightening thread.

Advantageously, the collar comprises an arm which can extend between the branches parallel to the rod and can participate in the mounting of the lock on the collar via the groove.

Advantageously, the arm comprises two parts which can extend on either side of the lock.

Advantageously, the two parts are spaced apart from each other.

Advantageously, at least one of the two parts comprises a slot.

Advantageously, the two parts are elastically deformable.

Advantageously, the two parts are connected to each other.

The invention also provides a combination of a collar and of a lock for an osteosynthesis system according to the invention, the collar comprising a flange, the lock being able to be mounted movably in rotation on the collar, and in which either one of the collar or the lock has a groove which can receive the other of the collar or the lock for mounting the lock on the collar, the collar and the lock having means of assembly for introducing the other of the collar or the lock into the groove.

Other characteristics and advantages of the invention will become clear from the following description of six preferred embodiments which are given as nonlimiting examples.

DETAILED DESCRIPTION

A first embodiment of the spinal osteosynthesis system according to the invention will be described with reference to FIGS. 1 through 4.

The system comprises vertebral anchoring members, here in the form of pedicle screws 2, each comprising a threaded body 4 and a head with two branches 6 extending at distance from and opposite each other. The two branches 6 constitute two sectors of the same cylinder coaxial to the body 4 of the screw. The outer cylindrical faces 8 of the branches are coaxial and smooth. The inner cylindrical faces 10 of the branches are coaxial and threaded. The system includes a smooth and rigid elongate rod 12 of circular cross section, and for each screw 2 a ring or olive 14 with a cylindrical inner face 15 substantially of the same radius as that of the rod 12 and with a convex spherical outer face 17 having the same radius as a concave spherical seat of the screw head between the branches 6. The ring 14 is slotted on one side parallel to its axis and can be received on the rod 12 by sliding adjustment. This assembly makes it possible to control the orientation of the rod 12 relative to the screw 2 in two mutually perpendicular planes, about a mean position of the rod. More details concerning these elements will be found in the documents FR-2 642 643 and FR-2 659 546 which are incorporated herein by reference.

For each screw 2, the system comprises a collar 16 and a lock 18. The collar 16 includes a lateral wall 20 constituting a flange or ring, with cylindrical outer 22 and inner 24 faces, which are here smooth. The inner face 24 has a radius approximately equal to that of the outer face 8 of the branches 6 in order to permit a sliding adjustment on these. The collar 16 is in this case a cap and includes, at an upper edge of the flange 20, a plane upper wall 26 perpendicular to the axis 29 of the flange and having at its center an orifice 28 provided with a thread which we will here call an introduction thread.

The lock 18 has an outer cylindrical face 30 of axis 29 and provided, along its entire length, and especially starting from a lower face 31 of the lock, with an introduction thread which can form a screw-nut connection with that 28 of the collar. The lock 18 has an annular groove 32 of U-shaped profile into which the threaded cylindrical face 30 opens. Parallel to the axis 29, this groove has a width which is slightly greater than the thickness of the upper wall 28 of the collar, so that this wall 28 can be received in the groove 32. On that side of the groove 32 opposite the cylindrical face 30, the lock has a circular and plane upper wall 34 perpendicular to the axis 29 and with a radius greater than that of the orifice 28 of the collar. A hexagonal socket 36 is formed in the lock starting from its upper face 38. The lock and the collar are generally symmetrical in revolution about their axis 29.

Figures 1, 4:
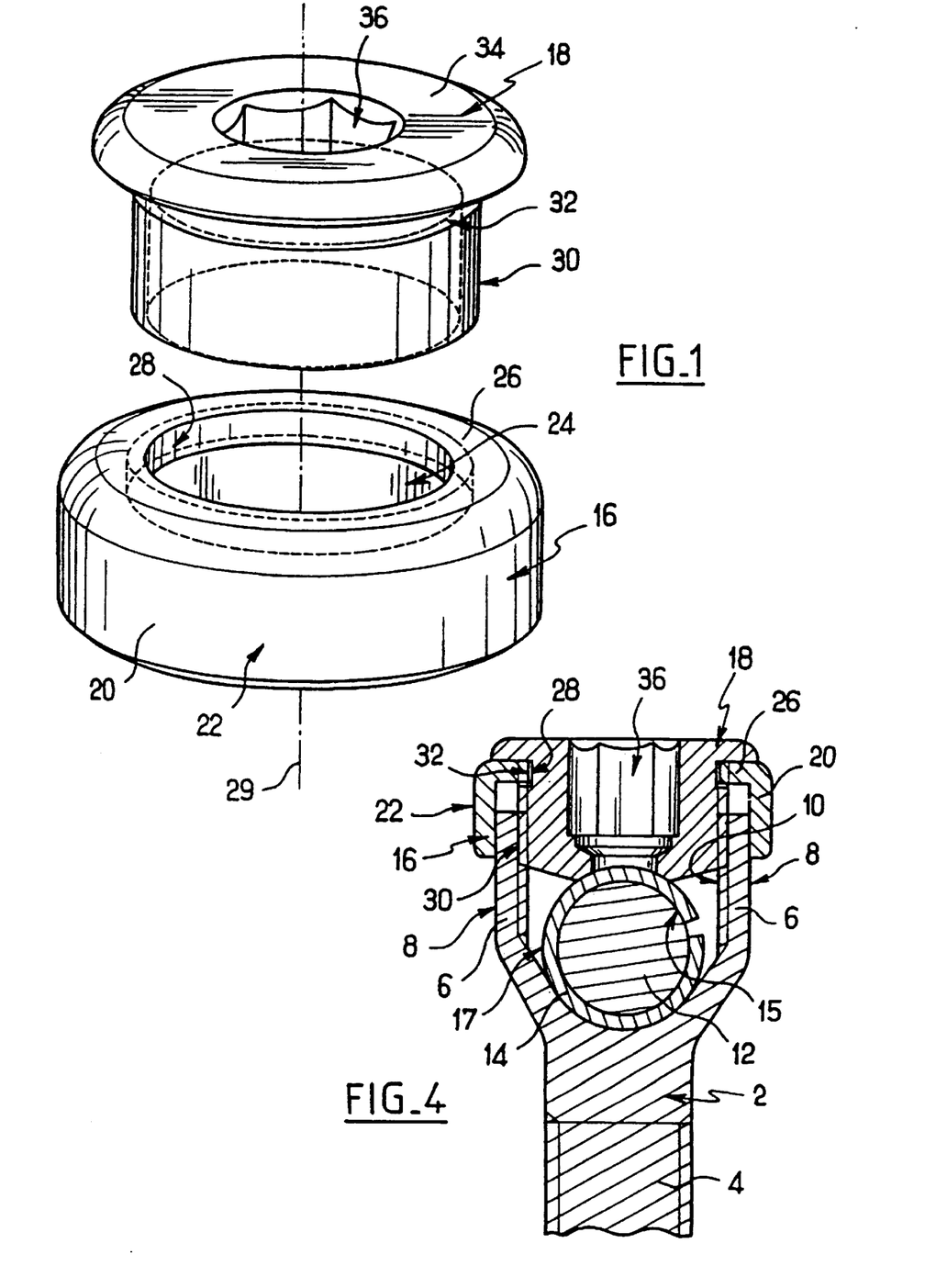
FIG. 1 is an exploded perspective view of lock and the collar according to a first embodiment of the invention.
FIG. 4 is a view analogous to FIG. 3, showing the lock and the collar on a pedicle screw.
Figure 2:
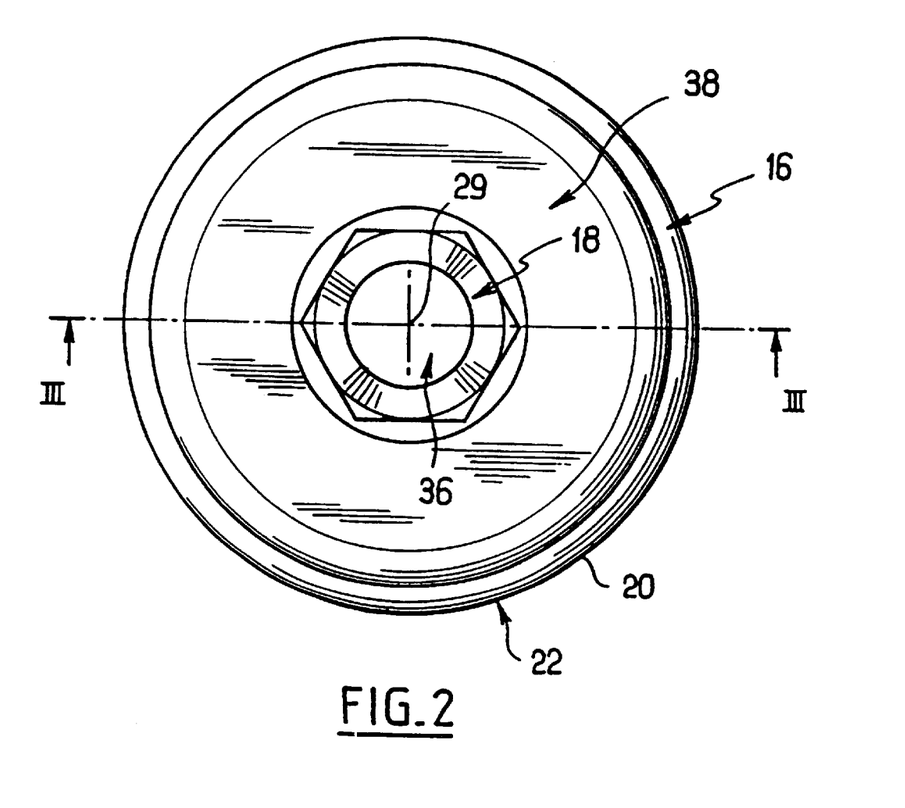
FIG. 2 is a plan view of the collar and of the lock from FIG. 1 when joined together.
Figure 3:
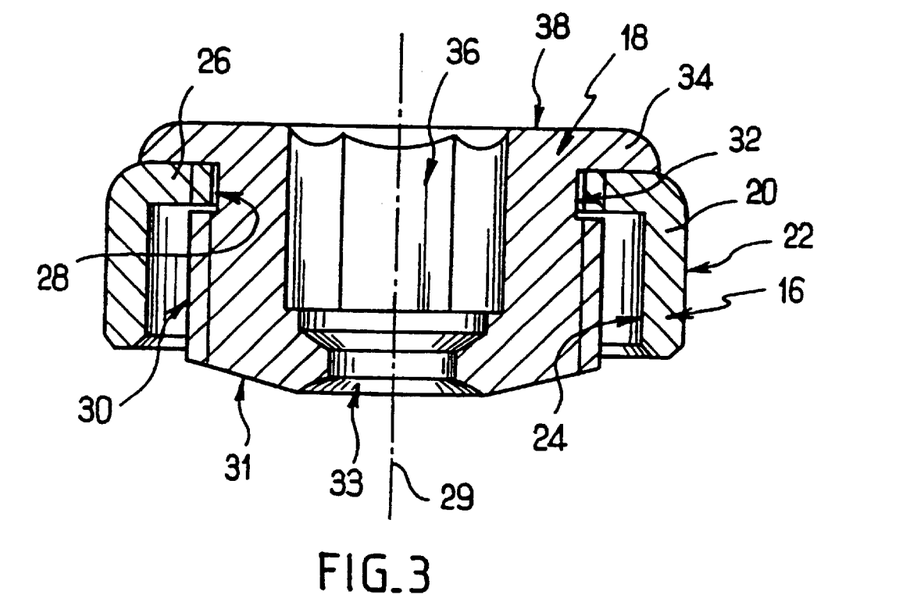
FIG. 3 is an axial cross section of the lock and of the collar when joined together, on the plane III—III in FIG. 2.

The lock 18 and the collar 16 being initially separate as shown in FIG. 1, in order to join them the lower face 31 of the lock is engaged in the orifice 28 of the collar to bring the two introduction threads 28 and 30 into engagement with each other. The screwing is continued until the wall 26 of the collar is introduced into the groove 32 of the lock. The mutual engagement of the introduction threads 28, 30 then ceases and the collar is rendered movable in rotation relative to the lock about their common axis 29 by being blocked in terms of sliding relative to the lock. In this position, the lateral wall 20 of the collar extends along its entire length opposite and at a distance from the introduction thread 30 of the lock. The introduction threads 28, 30 are here arranged such that the introduction thread 30 of the lock can come into engagement with the tightening thread 10 of the branches 6 and in so doing serves as a tightening thread. Consequently, the introduction thread 28 of the collar has the same characteristic dimensions as the branches 6.

During an intervention, each pedicle screw 2 is fitted on a vertebra, then the rod 12 is inserted with the ring 14 between the branches 6. The lock 18 and the collar 16 having been joined together beforehand as indicated above, the collar 16 is brought to the upper end of the branches 6 and the lock 18 is screwed between them, the introduction thread 30 of the lock cooperating with the tightening thread 10 of the branches 6. As the lock 18 descends, the collar 16 follows the latter by sliding on the outer face 8 of the branches 6. The lower end 31 of the lock, the lowest part of which is a circular edge delimiting a spherical concave face 33, comes into contact with the convex spherical outer face 17 of the ring 14 before the upper end edges of the branches 6 abut against the lower face of the upper wall 26 of the collar. By virtue of the collar which prevents mutual spacing apart apart of the branches 6, the lock 8 is then clamped on the ring 14 in order to block the rod 12 in the ring in the chosen angular orientation at the bottom of the head of the pedicle screw.

Figure 5:
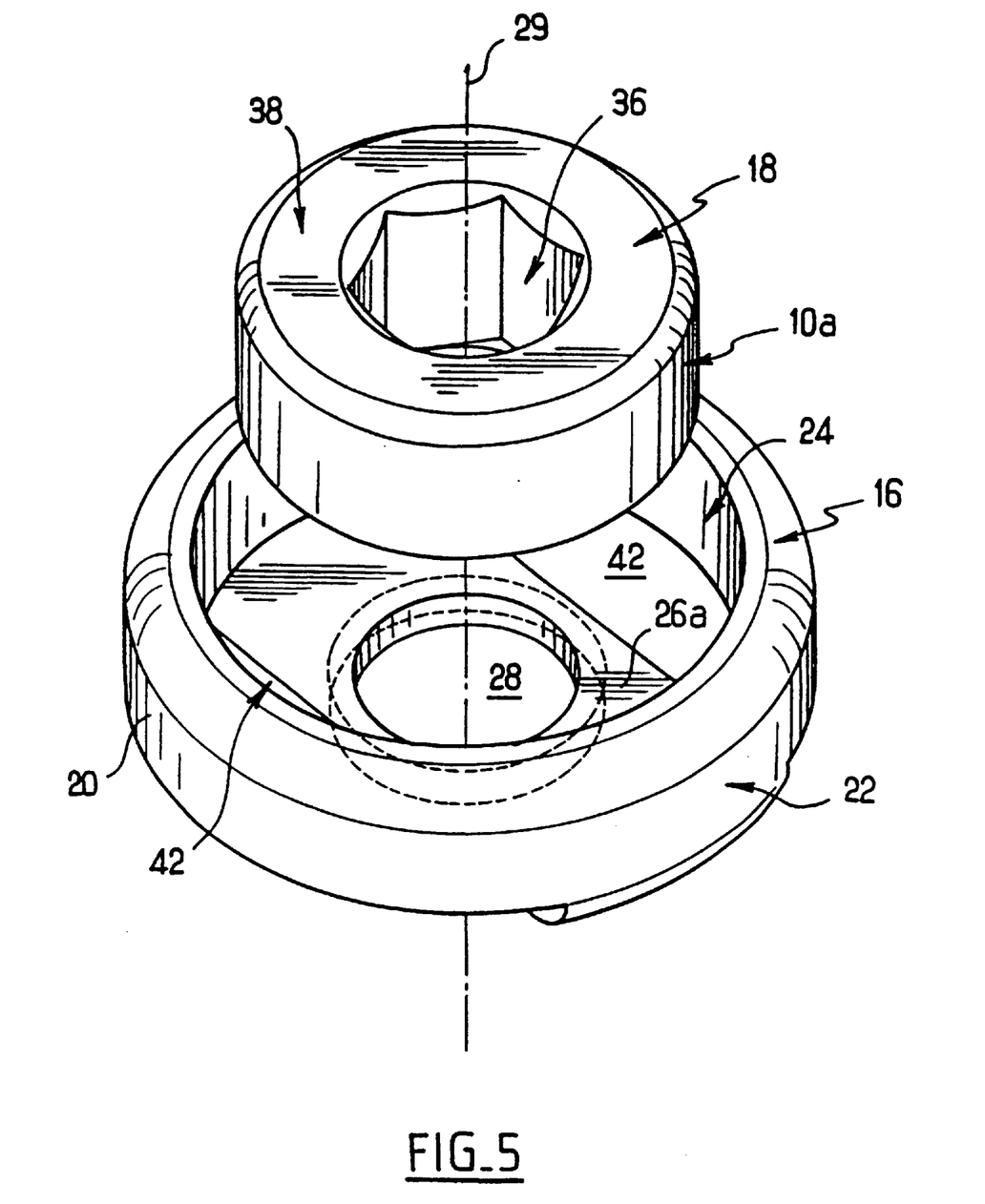
FIG. 5 is a view analogous to FIG. 1, showing a second embodiment.
Figure 6:
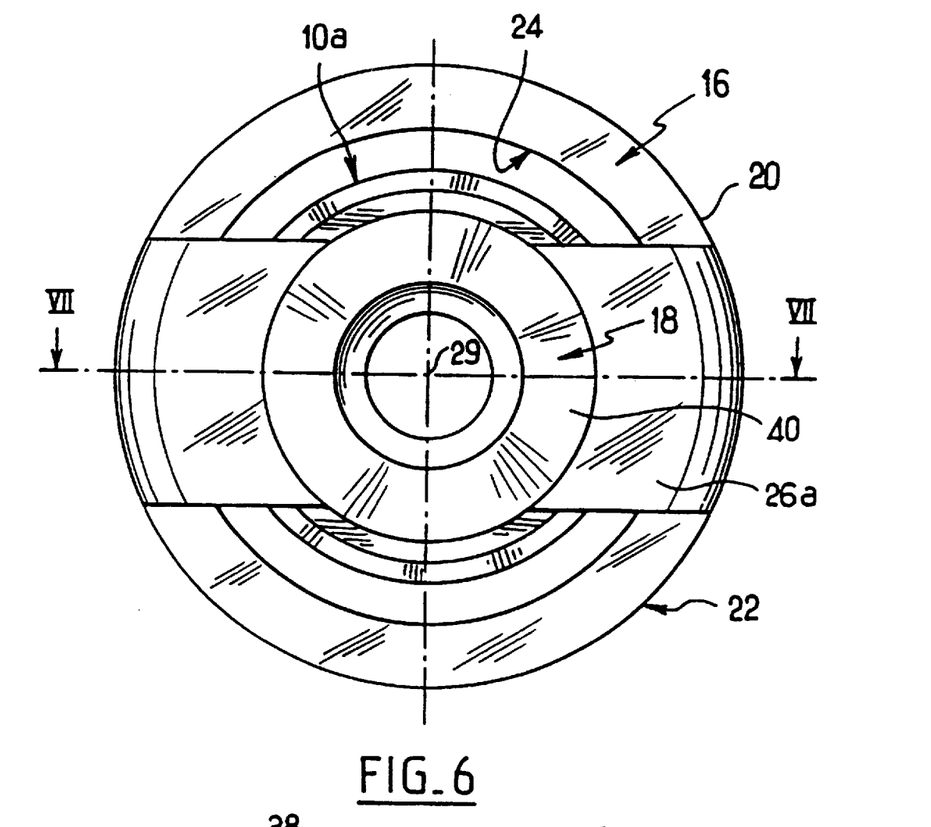
FIG. 6 is a bottom view of the lock and of the collar from FIG. 5 when joined together.
Figure 7:
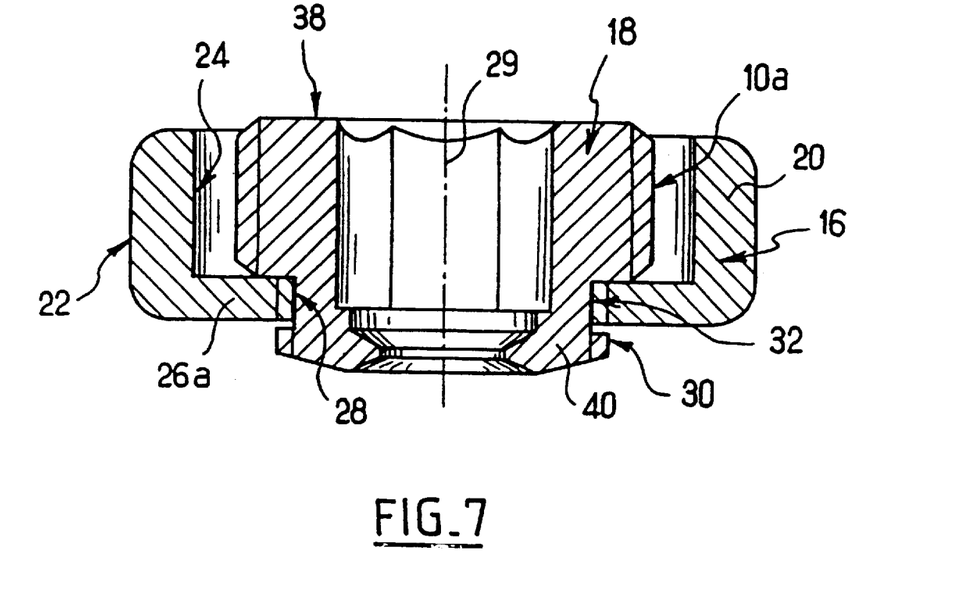
FIG. 7 is an axial cross section of the lock and of the collar on the plane VII—VII in FIG. 6.

In the second embodiment illustrated in FIGS. 5 through 7, the upper wall 26 of the collar is replaced by an arm 26a of a generally plane rectangular shape extending perpendicular to the axis of the collar, diametrically from one edge to the other of its lateral wall 20. The arm 26a is contiguous with a lower edge of the lateral wall 20. It has the threaded orifice 28 at its center. The arm 26a thus delimits two openings 42 having a rectilinear inner edge formed by the arm 26a and a circular outer edge formed by the cylindrical wall 20 of the collar, here similar to a ring. These openings 42 can receive the respective branches 6, between which the arm can thus itself be inserted parallel to the rod 12.

On the lock 18, the threaded outer cylindrical face 10a now extends from the upper face 38 of the lock to the groove 32 situated under the latter. The upper wall 34 is replaced by a lower wall 40 contiguous to the groove, of which it forms a flank. The radius of this lower wall 40 is greater than that of the bottom of the groove 32 and less than that of the outer cylindrical face 10a. The lower wall 40 has, on its perimeter, an introduction thread 30 which can cooperate with that 28 of the lower wall 26a of the collar. These introduction threads 28, 30 here have a radius different than those of the clamping threads 10 of the branches 6 and 10a of the lock, so that they cannot cooperate with these.

To join the collar 16 and the lock 18 together, the lower wall 40 of the lock is introduced, opposite the cylindrical lateral wall 20 of the collar, into the orifice 28 of the arm 26a. The lock is then screwed into this orifice until the arm is lodged in the groove 32 and an assembly is obtained analogous to that described in the first embodiment.

This combination is placed on the pedicle screw 2 by introducing the upper end edges of the branches 6 into the openings 42. The clamping threads 10 of the branches then come into engagement with that 10a of the lock. The lock is then maneuvered in order to cause it to descend in the direction of the rod 12, with the collar 16 whose cylindrical lateral wall 20 follows the lock outside the branches 6 and the arm 26a follows the lock between the branches. At a certain stage the branches 6 can emerge projecting from the upper parts the collar and of the lock, between these. The groove 32 is this time between the clamping thread 10a of the lock and the rod 12. The assembly is clamped as in the first embodiment.

Figure 8:
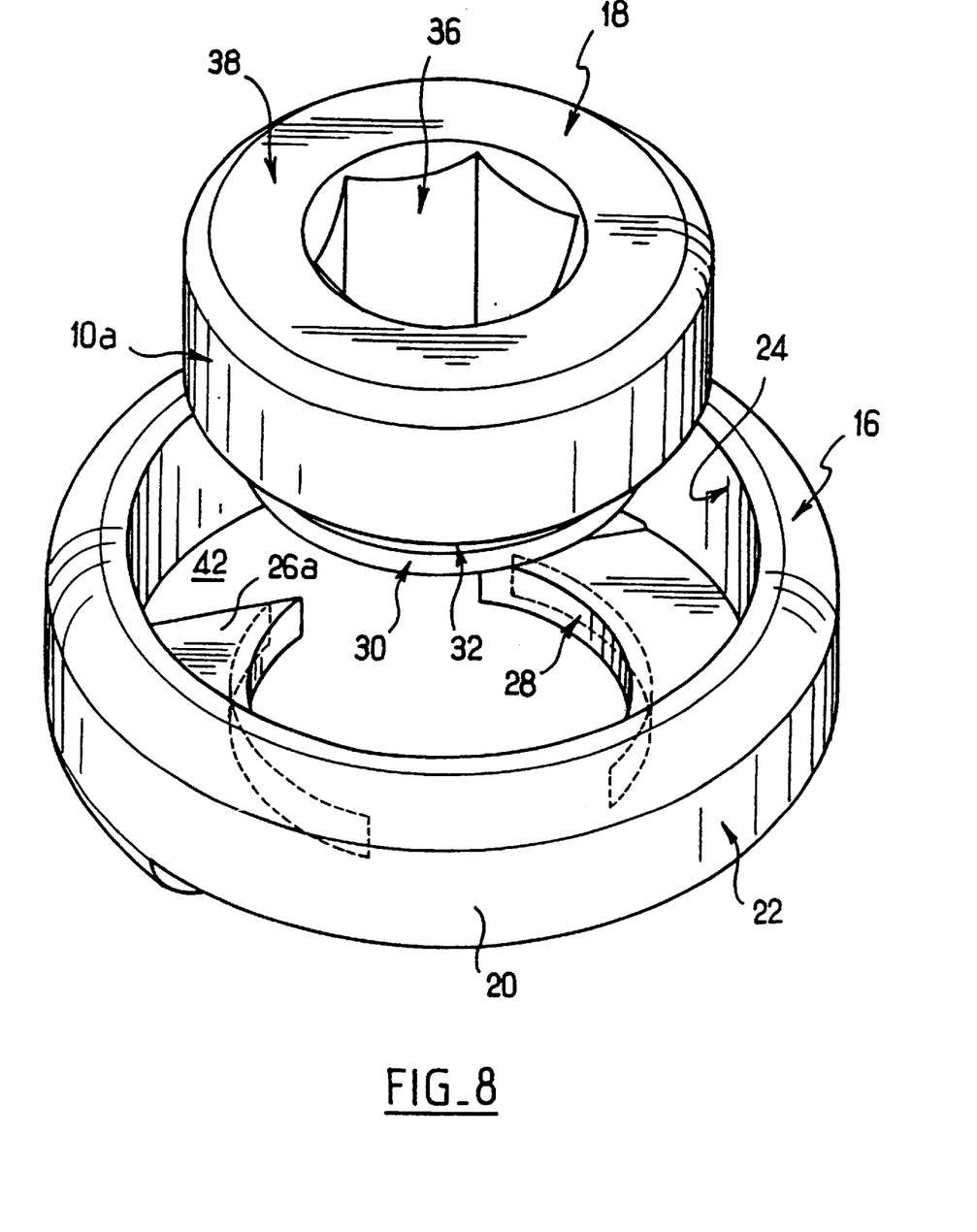
FIG. 8 is a view analogous to FIG. 1, showing a third embodiment.

The third embodiment illustrated in FIG. 8 constitutes a variant of the second embodiment. Here, the diameter of the orifice 28 of the arm 26a is greater than the width of the arm of the openings 42. The two portions of the arm 26a which are situated on either side of the axis of the collar are therefore no longer connected to each other, as in FIG. 5, but spaced apart. The orifice 28 communicates this time with the two openings 42. The functioning of the system for joining the collar to the lock and mounting them on the screw is unchanged.

Figure 9:
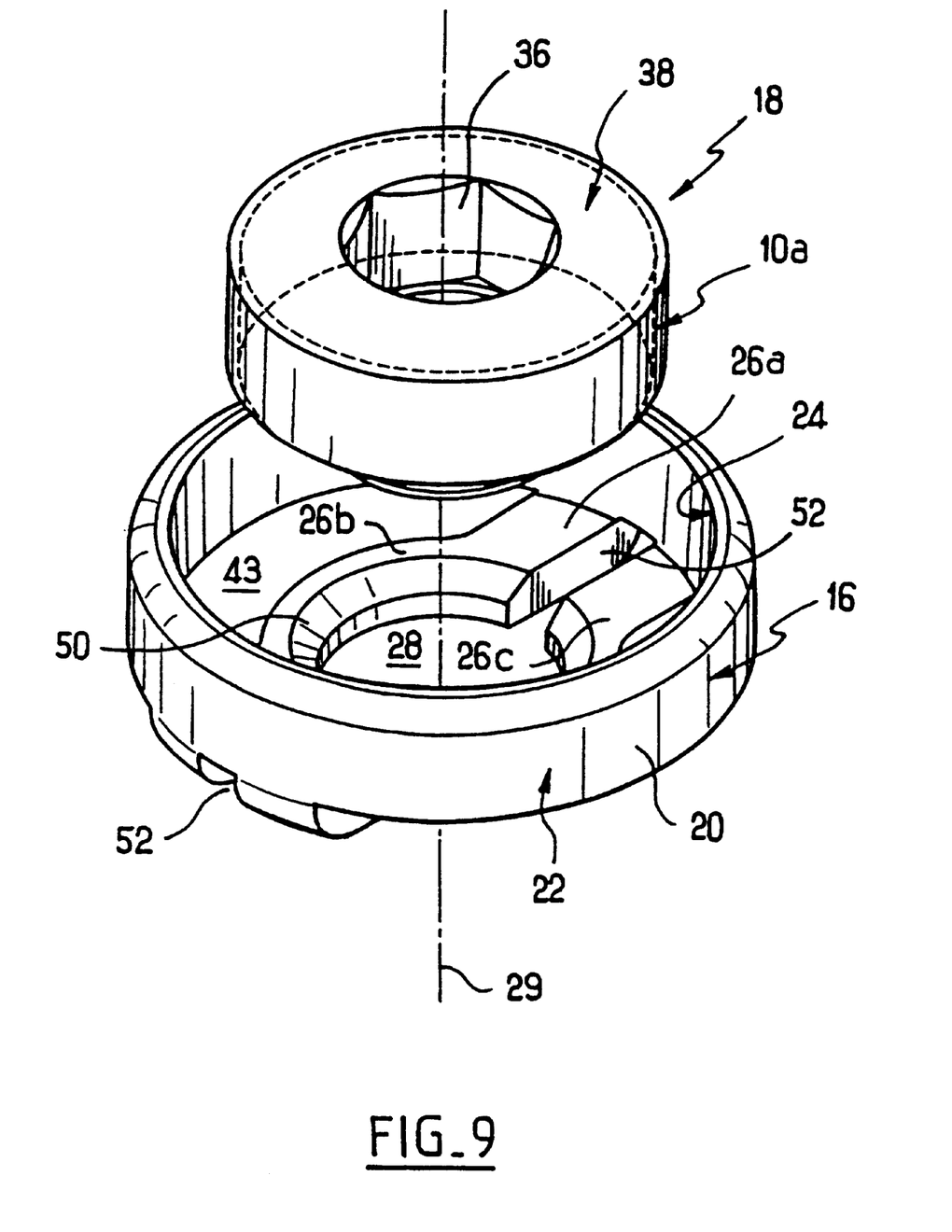
FIG. 9 is an exploded perspective plan view of a fourth preferred embodiment.
Figure 10:
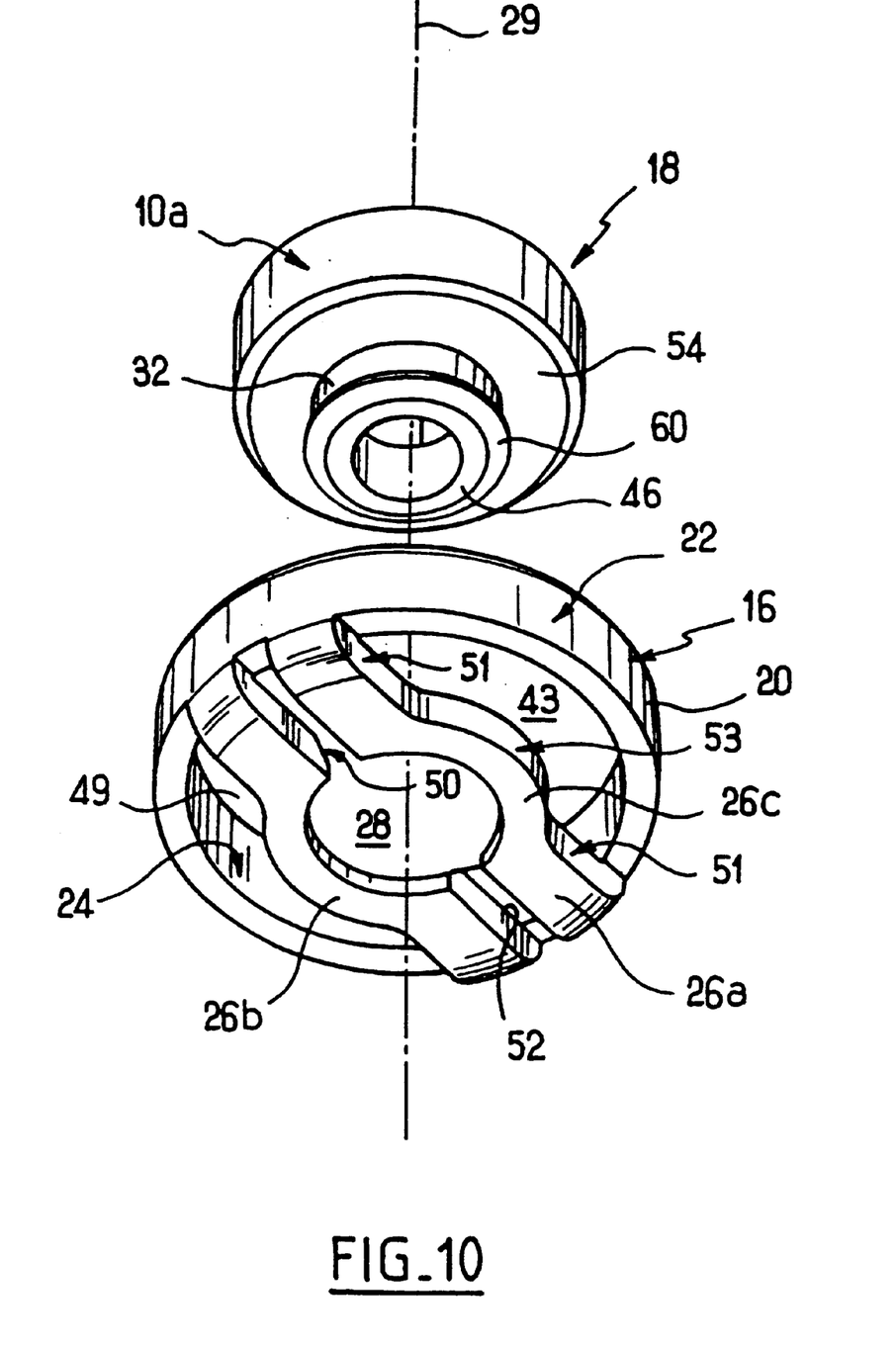
FIG. 10 is an exploded perspective bottom view of the fourth embodiment.
Figure 11:
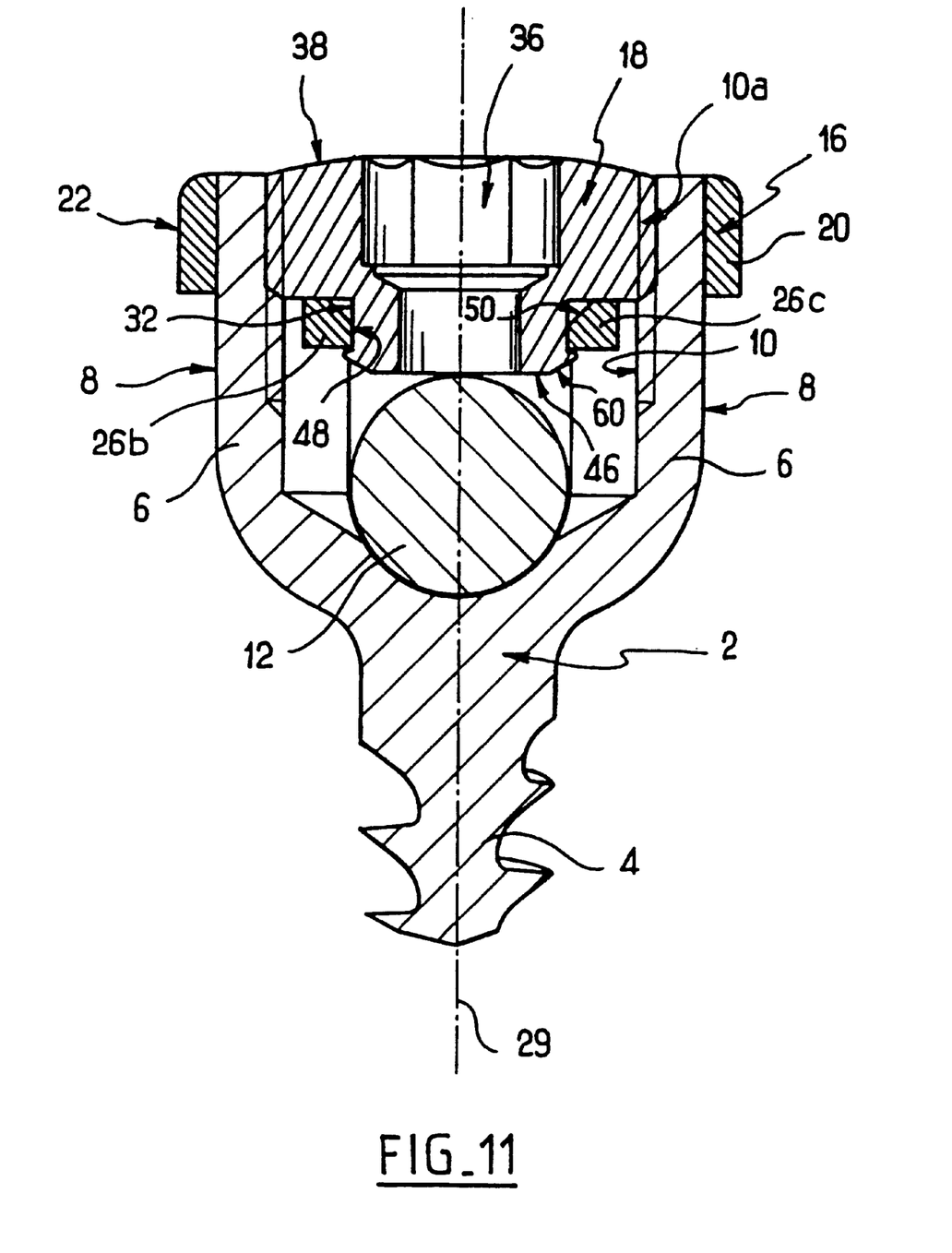
FIG. 11 is an axial cross section of the fourth embodiment mounted on an anchoring member.

In a fourth embodiment of the spinal osteosynthesis system according to the invention, with reference to FIGS. 9 through 11, the collar 16 includes an arm 26a similar to that of the second embodiment mentioned above, in two parts 26b and 26c. It has a smooth orifice 28 including an introduction chamfer 50. A slot 52 separates the two parts 26b and 26c of the arm 26a. This slot 52 is parallel to the median axis of the arm 26a and is placed in such a way that the parts 26b and 26c are symmetrical in mirror image. The arm 26a thus delimits two openings 43 having a circular outer edge formed by the cylindrical wall 20 of the collar 16 which is here similar to a ring, and an inner edge having two plane faces 51 separated by a circular face 53 coaxial to the cylindrical wall 20. These openings 43 can receive the respective branches 6, between which the arm can thus itself be inserted parallel to the rod 12.

As in the embodiment in FIG. 7, the lock 18 has a lip 60, called the introduction lip, which is unthreaded and extends from the bottom of the groove and is surmounted by the annular groove 32 of U-shaped profile. The shape of the lip 60 complements the introduction chamfer 50 of the orifice 28 of the collar 16. The groove 32 has, parallel to the axis 29, a width which is slightly greater than the thickness of the arm 26a of the collar, so that this arm can be received in the groove 32. On the side of the groove 32 opposite the introduction lip 60, the lock has a plane upper wall 54 which is circular and perpendicular to the axis 29 and has a radius greater than the orifice 28 of the collar 16.

As in the abovementioned embodiments, the lock 18 and the collar 16 are initially separate as in FIGS. 9 and 10. To join them together, the lower face 46 of the lock is engaged in the orifice 28 of the collar to bring the introduction lip 60 and the chamfer 50 into contact. A stress is applied along the axis 29, the introduction lip 60 spaces the two parts 26b and 26c apart elastically and by sliding on the chamfer 50. The elastic deformation ceases when the arm 26 of the collar is introduced into the groove 32 of the lock. The collar is then rendered movable in rotation relative to the lock, about their common axis 29, by being blocked in terms of sliding relative to the lock. In this position, the wall 20 of the collar extends over the entire length opposite and at a distance from the thread 10a of the lock.

Figure 12:
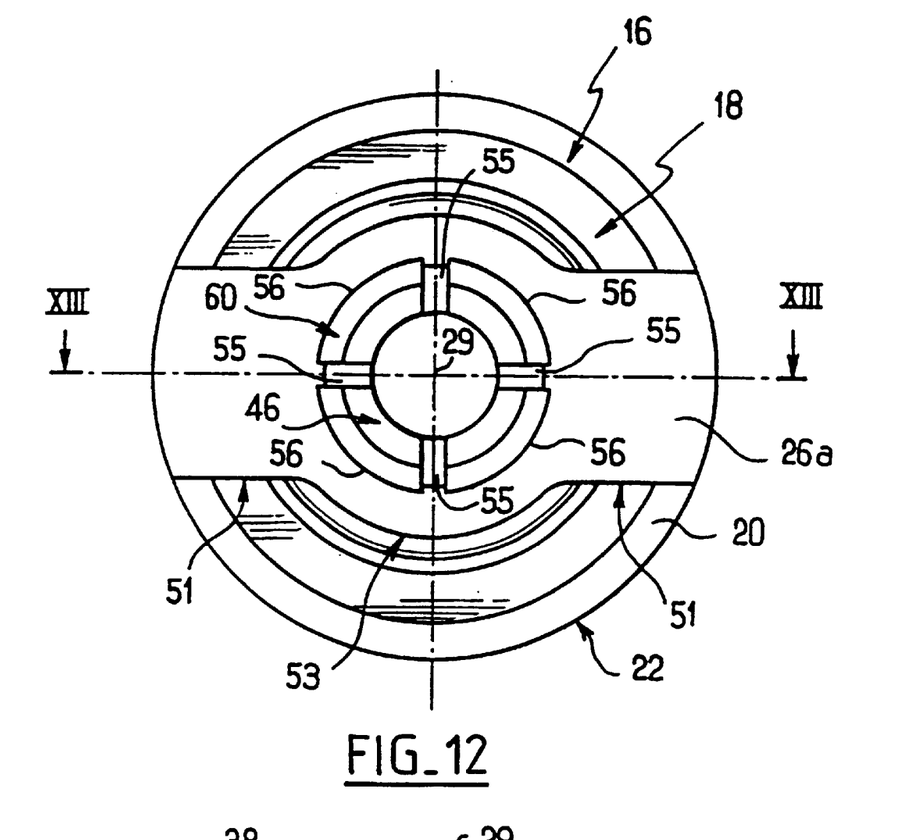
FIGS. 12 and 13 are a bottom view and an axial cross section along XIII—XIII of a fifth embodiment.
Figure 13:
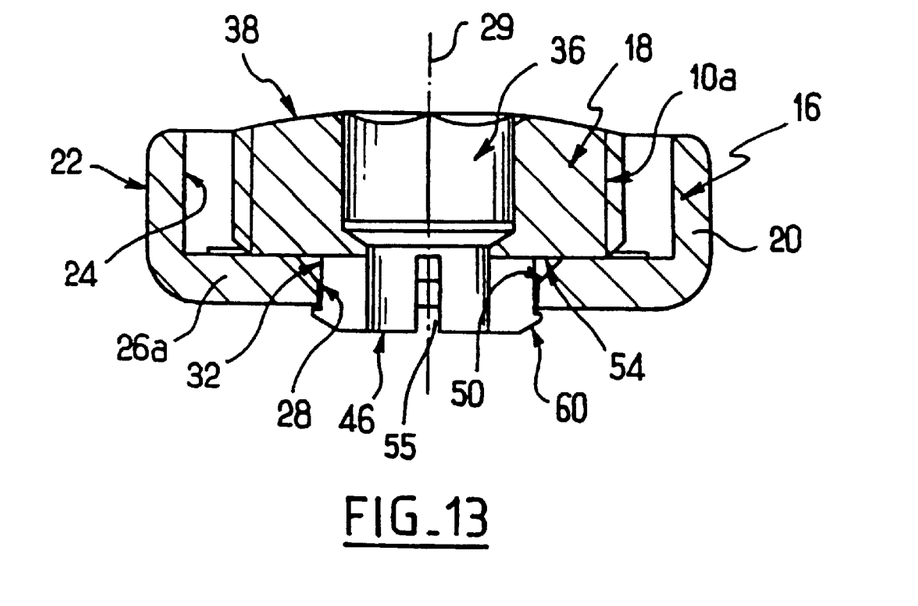

In a fifth embodiment illustrated in FIGS. 12 and 13, the arm 26a is monobloc and no longer comprises a slot 52. The lock 18 is identical to the embodiment previously described, except that it includes at least one radial slot 55 extending from the end face 46 of the lock to the wall 54 of said lock and as far as the recessed core of the lock. In a preferred embodiment which is illustrated, the lock 18 includes four radial slots 55 which are arranged at 90° and whose median axes intersect on the axis 29. The part of the lock 18 including the groove 32 and the introduction lip 60 is thus divided into four identical sectors 56. The lock 18 is joined to the collar 16 in the same way, except as regards the elastic deformation which is no longer supported by the arm 26a but by the sectors 56 of the 18. The mounting of said assembly on the pedicle screw 2 is identical.

Figure 14:
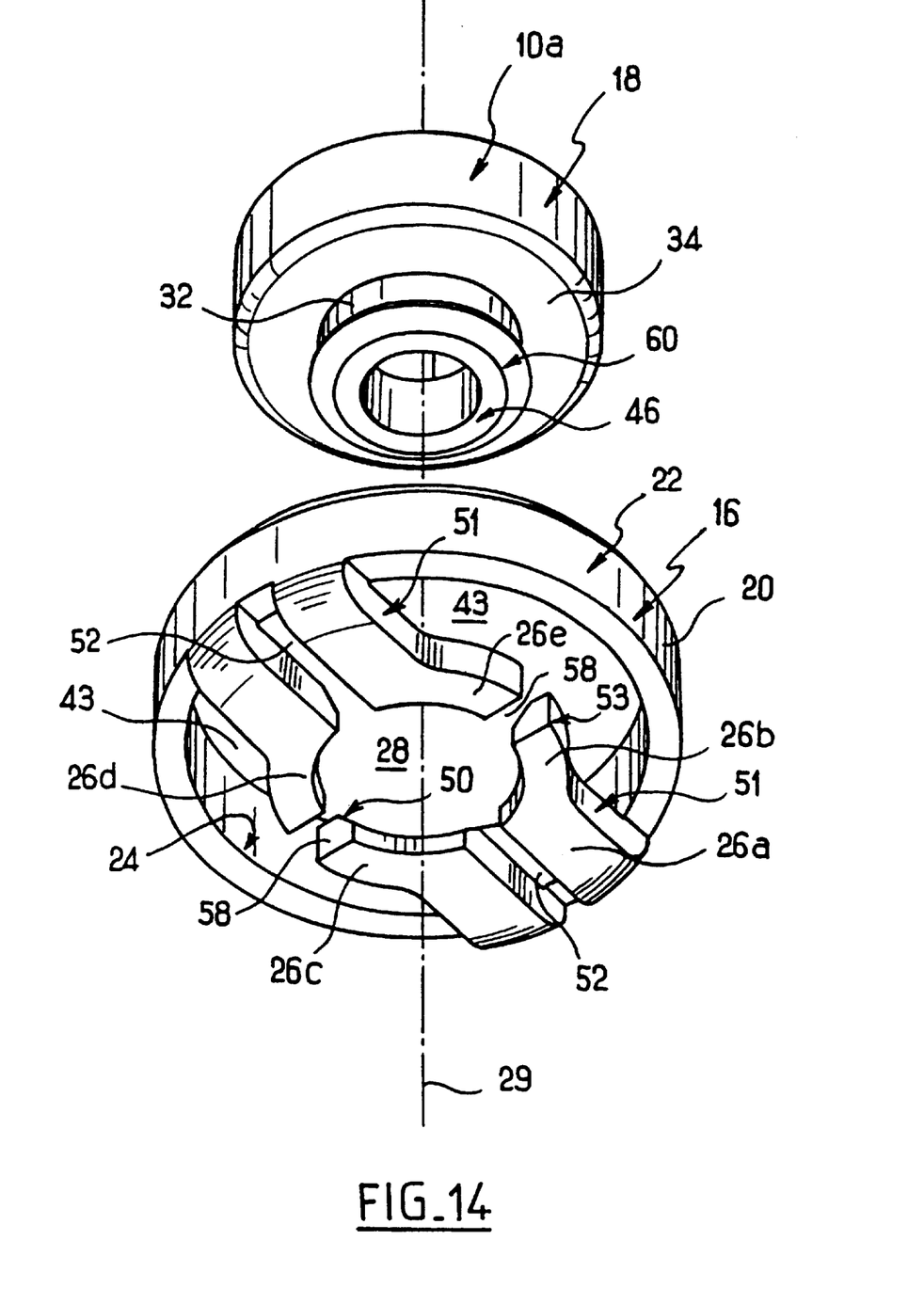
FIG. 14 is an exploded perspective view of a sixth embodiment.

The sixth embodiment illustrated in FIG. 14 constitutes a variant of the fourth embodiment. The lock 18 is unchanged. On the collar 16, the arm 26a includes a supplementary slot 58 which is perpendicular to the slot 52 and whose intersection of the median axes is situated on the axis 29. The arm 26a is made up of four parts 26b, 26c, 26d and 26e which are symmetrical in pairs. The joining of the lock to the collar and the mounting on the pedicle screw 2 are identical to those described for the fourth embodiment.

It should be noted that FIG. 11 illustrates a variant for mounting the system of the present invention on an anchoring member which does not have a ring or olive 14 as intermediate component between the lock 18 and the rod 12, as illustrated in FIG. 4.

Of course, numerous modifications can be made to the invention without departing from the scope thereof.

The groove can be formed on the collar.

The anchoring members can be hooks.

The arm can extend on one side only of the lock.

The tightening thread cooperating with that of the branches can be on the collar and not on the lock. In this case, the collar permits screwing on the screw head and the lock prevents closing-together of the branches.

What is claimed is:

1. A spinal osteosynthesis system comprising:
   a rod;
   a vertebral member comprising two branches which can receive the rod between them;
   a collar which can prevent the branches from being spaced apart; and
   a lock which can clamp the rod and can be mounted movably in rotation on the collar;
   wherein either one of the collar or the lock has a groove which can receive the other of the collar or the lock for mounting the lock on the collar; and
   wherein the collar and the lock have introduction threads for introducing the other of the collar or the lock into the groove.

2. The system of claim 1, wherein either one of the collar or the lock is elastically deformable for introducing said other of the collar of the lock into the groove.

3. The system of claim 2, wherein the lock comprises the groove.

4. The system of claim 3, wherein the lock comprises at least one slot at the level of the groove.

5. The system of claim 1, wherein a first of the collar or lock has a tightening thread which can cooperate with a tightening thread of the branches, a second of the collar or the lock extending opposite the tightening thread of the first.

6. The system of claim 5, wherein the tightening thread of the first is one of the introduction threads.

7. The system of claim 6, wherein the tightening thread extends between the groove and the rod.

8. The system of claim 6, wherein the groove extends between the rod and the tightening thread.

9. The system of claim 1, wherein the collar comprises an arm which can extend between the branches parallel to the rod and can participate in the mounting of the lock on the collar via the groove.

10. The system of claim 9, wherein the arm comprises two parts which extend on either side of the lock.

11. The system of claim 10, wherein the two parts are spaced apart from each other.

12. The system of claim 10, wherein the two parts are elastically deformable.

13. The system of claim 10, wherein at least one of the two parts comprises a slot.

14. The system of claim 10, wherein the two parts are connected to each other.

15. The system of claim 2, wherein the two parts are connected to each other.

16. A spinal osteosynthesis system comprising:

a rod;

a vertebral member comprising two branches which can receive the rod between them;

a collar which can prevent the branches from being spaced apart; and a lock which can clamp the rod and can be mounted movably in rotation on the collar;

wherein either one of the collar or the lock has a groove which can receive the other of the collar or the lock for mounting the lock on the collar; and wherein the collar comprises, an arm which can extend between the branches parallel to the rod, can participate in the mounting of the lock on the collar via the groove, and can prevent rotation of the collar relative to the vertebral member.

17. The system of claim 16, wherein either one of the collar or the lock is elastically deformable for introducing said other of the collar of the lock into the groove.

18. The system of claim 17, wherein the lock comprises the groove.

19. The system of claim 18, wherein the lock comprises at least one slot at the level of the groove.

20. The system of claim 16, wherein the collar and the lock have introduction threads for introducing the other of the collar or the lock into the groove.

21. The system of claim 20, wherein a first of the collar or the lock has a tightening thread which can cooperate with a tightening thread of the branches, a second of the collar or the lock extending opposite the tightening thread of the first.

22. The system of claim 21, wherein the tightening thread of the first is one of the introduction threads.

23. The system of claim 22, wherein the tightening thread extends between the groove and the rod.

24. The system of claim 22, wherein the groove extends between the rod and the tightening thread.

25. The system of claim 16, the arm comprises two parts which extend on either side of the lock.

26. The system of claim 25, wherein the two parts are spaced apart from each other.

27. The system of claim 25, wherein the two parts are elastically deformable.

28. The system of claim 25, wherein at least one of the two parts comprises a slot.

29. A spinal osteosynthesis system comprising:

a rod;

a vertebral member comprising two branches which can receive the rod between them;

a collar which can prevent the branches from being spaced apart; and a lock which can clamp the rod and can be mounted movably in rotation on the collar;

wherein the lock has a groove which can receive the collar for mounting the lock on the collar, and at least one slot at the level of the groove; and wherein either one of the collar or the lock is elastically deformable for introducing said other of the collar of the lock into the groove.

30. The system of claim 29, wherein the collar and the lock have introduction threads for introducing the other of the collar or the lock into the groove.

31. The system of claim 30, wherein a first of the collar or the lock has a tightening thread which can cooperate with a tightening thread of the branches, a second of the collar or the lock extending opposite the tightening thread of the first.

32. The system of claim 31, wherein the tightening thread of the first is one of the introduction threads.

33. The system of claim 32, wherein the tightening thread extends between the groove and the rod.

34. The system of claim 32, wherein the groove extends between the rod and the tightening thread.

35. The system of claim 30, wherein the collar comprises an arm which can extend between the branches parallel to the rod and can participate in the mounting of the lock on the collar via the groove.

36. The system of claim 35, wherein the arm comprises two parts which extend on either side of the lock.

37. The system of claim 36, wherein the two parts are spaced apart from each other.

38. The system of claim 36, wherein the two parts are elastically deformable.

39. The system of claim 36, wherein at least one of the two parts comprises a slot.

40. The system of claim 36, wherein the two parts are connected each other.

\* \* \* \* \*

UNITED STATES PATENT AND TRADEMARK OFFICE
CERTIFICATE OF CORRECTION

PATENT NO.      : 6,585,737 B1                                         Page 1 of 1
DATED           : July 1, 2003
INVENTOR(S)     : Christian Baccelli, Fabien Gauchet and Cécile Vienney It is certified that error appears in the above-identified patent and that said Letters Patent is hereby corrected as shown below:

<u>Title page, Item [54] and Column 1, line 1,</u>
Title, "BACKBONE" should read -- SPINAL --.

<u>Column 4,</u>
Line 13, cancel "apart" (second occurrence).

<u>Column 6,</u>
Line 35, "of" (second occurrence) should read -- or --.
Line 64, "2" should read -- 10 --.

<u>Column 7,</u>
Line 19, "of" (second occurrence) should read -- or --.
Line 37, after "16" insert -- wherein --.

<u>Column 8,</u>
Line 13, "of" (second occurrence) should read -- or --.
Line 28, "30" should read -- 29 --.
Line 41, after "connected" insert -- to --.

Signed and Sealed this

Ninth Day of December, 2003

JAMES E. ROGAN
*Director of the United States Patent and Trademark Office*